(12) United States Patent
Neuber et al.

(10) Patent No.: US 12,239,468 B2
(45) Date of Patent: Mar. 4, 2025

(54) PATIENT COUCH FOR A MEDICAL IMAGING INSTALLATION

(71) Applicant: Siemens Healthcare GmbH, Erlangen (DE)

(72) Inventors: Wolfgang Neuber, Pressath (DE); Matthias Mueller, Bamberg (DE); Guenther Gambke, Weidenberg (DE); Andreas Deinlein, Bayreuth (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 801 days.

(21) Appl. No.: 17/393,559

(22) Filed: Aug. 4, 2021

(65) Prior Publication Data

US 2022/0047218 A1 Feb. 17, 2022

(30) Foreign Application Priority Data

Aug. 11, 2020 (DE) .................... 20 2020 104 652.7

(51) Int. Cl.
*A61B 5/00* (2006.01)
*A61B 5/055* (2006.01)

(52) U.S. Cl.
CPC .............. *A61B 5/70* (2013.01); *A61B 5/055* (2013.01); *A61B 5/742* (2013.01); *A61B 2560/0456* (2013.01); *A61B 2562/0204* (2013.01); *A61B 2562/0219* (2013.01); *A61B 2562/0223* (2013.01)

(58) Field of Classification Search
CPC ...... A61B 5/704; A61B 6/547; A61G 2203/22
See application file for complete search history.

(56) References Cited

U.S. PATENT DOCUMENTS

| 4,671,728 A * | 6/1987 | Clark | A61B 6/0487 414/284 |
| 11,491,063 B2 * | 11/2022 | Takamura | A61B 5/055 |
| 2005/0020906 A1 * | 1/2005 | Seijger | A61B 5/055 5/601 |
| 2006/0167356 A1 * | 7/2006 | Everett | A61B 6/0487 600/407 |
| 2011/0154569 A1 * | 6/2011 | Wiggers | A61N 5/1049 5/81.1 R |

(Continued)

FOREIGN PATENT DOCUMENTS

| DE | 202016007430 U1 | 1/2017 |
| DE | 102016203304 A1 * | 9/2017 |
| DE | 102018203014 A1 * | 8/2019 |

*Primary Examiner* — Eric J Kurilla
(74) *Attorney, Agent, or Firm* — Harness, Dickey & Pierce, P.L.C.

(57) ABSTRACT

A patient couch is disclosed. In an embodiment, the patient couch includes a docking facility for mechanical docking on a docking point of a medical imaging installation; a drive unit including a plurality of wheels for a drive movement of the patient couch up to a docking position, where the docking facility reaches the docking point; at least one sensor, to acquire sensor signals characterizing a relative position between the medical imaging installation and the patient couch; a computing unit to calculate a movement trajectory with a destination of the docking position for the patient couch, based on the sensor signals acquired; and a display facility, to display the movement trajectory calculated for a user.

21 Claims, 5 Drawing Sheets

(56) References Cited

U.S. PATENT DOCUMENTS

| | | | | |
|---|---|---|---|---|
| 2014/0303477 A1* | 10/2014 | Sunazuka | ............ | A61B 6/0407 |
| | | | | 600/407 |
| 2014/0331406 A1* | 11/2014 | Haider | ................. | A61G 13/128 |
| | | | | 701/23 |
| 2015/0007390 A1* | 1/2015 | Haider | ..................... | A61G 1/04 |
| | | | | 5/600 |
| 2018/0317804 A1* | 11/2018 | Dumoulin | .............. | A61G 7/103 |
| 2018/0329422 A1* | 11/2018 | Biber | .................... | G05D 1/0088 |
| 2021/0068701 A1* | 3/2021 | Piron | ................... | A61B 5/0036 |
| 2022/0008016 A1* | 1/2022 | Harrison | ................ | A61G 3/001 |

* cited by examiner

PATIENT COUCH FOR A MEDICAL IMAGING INSTALLATION

PRIORITY STATEMENT

The present application hereby claims priority under 35 U.S.C. § 119 to German patent application number DE 202020104652.7 filed Aug. 11, 2020, the entire contents of which are hereby incorporated herein by reference.

FIELD

Example embodiments of the invention generally relate to a patient couch with a docking facility, which is embodied to determine a movement trajectory up to a docking point in a medical imaging installation.

BACKGROUND

Mobile patient couches are basically known. First, these can interact with a medical imaging installation during an image data acquisition or also be moved separate from the imaging installation.

In order to facilitate the moving or driving of the patient couch, the chassis of the mobile patient couch can comprise, for example, four freely rotatable casters each on one corner of the patient couch and a fifth wheel arranged centrally in the middle between the casters and oriented in a straight direction. This fifth wheel is pushed against the ground by a spring mechanism and functions as a guide wheel. In a manual operating mode of the patient couch, the fifth wheel allows simple pushing straight ahead or round tight bends and in a stationary position allows a rotation of the patient couch around the fifth wheel. The fifth wheel can alternatively be equipped for a motor-assisted or autonomous operating mode of the patient couch with a drive motor, which can provide motor-assistance for or autonomously effect the pushing of the patient couch.

Hitherto it has been the responsibility of the operator to specify the direction of the movement of the couch by rotating the patient couch around the fifth wheel. The four casters orientate themselves according to the direction specified by the operator and follow the manual specification. Such a patient couch is known, for example from the German utility model specification DE 202016007430.

Such mobile patient couches therefore offer the option of placing a patient on the patient couch outside an examination room, that is, separate from the medical imaging installation, and/or for example, of attaching the coils that are optionally required for image data acquisition for a magnetic resonance examination (such as head, extremity or body coils).

Next, the mobile patient couch has to be brought to the medical imaging installation. For this purpose, as mentioned in the introduction, an operator has to push the patient couch, together with the patient located thereon, into the examination room and then, oriented as well as possible, onto a docking point in the medical imaging installation or the patient couch has to drive autonomously onto the docking point.

The patient couch has to be driven onto the docking point at the slowest possible speed, such that a jerky impact can be prevented or avoided as far as possible.

For operation in the medical imaging installation, the patient couch has a docking facility comprising a docking pin. In order for a docking process to be able to start at all, and optionally to be mechanically or hydraulically assisted, the patient couch and in particular the docking pin of the docking facility, have to be brought up to the docking point with an orientation that is within an angle of acceptance of from −7° to +7°. Ideally, when driving up, an orientation within an angle of from −2° to +2° should be achieved in order to minimize a sideways jerk due to an automatic further orientation of the patient couch to 0° during the docking process.

If the docking point on the medical imaging installation is arranged only a little above the floor of the examination room, the operator often does not have a direct view onto the docking pin of the docking facility or the docking point, since their field of view is obscured by the patient couch, by the patient and/or by accessories such as coils. A current distance or a lateral orientation or angular position between the patient couch and the docking point therefore has to be estimated by the operator.

Due to the selection of what is known to be a large acceptance angle of from −7° to +7°, it is possible in most cases for the operator to reach the docking point without an adequate view such that the docking process can be started by operating a button on the operating panel on the couch. By way of the docking process, the patient couch is pulled closer to the medical imaging installation with the aid of a drive in the docking point.

If it is not possible to approach the docking point within the specified tolerance range, appropriate feedback is sent to the operator by the medical imaging installation (along the lines of "Docking not possible"). The action of pushing the patient couch onto the docking point has to be repeated.

The inconvenience for the patient due to the likely initial impact, jerky lateral movements when docking/orientating and the necessary possible repetitions of pushing the couch into place have had to be tolerated until now, however.

SUMMARY

At least one embodiment of the present invention provides alternative devices/methods that make it possible to increase patient comfort when adjusting a mobile patient couch and improve ease of operation. In particular, at least one embodiment of the present invention provide devices/methods that facilitate a reliable and precise positioning of the patient couch on a docking point in a medical imaging installation.

Embodiments of the present invention are directed to a patient couch, and a medical imaging system comprising the patient couch. Preferred and/or alternative, advantageous embodiment variants form the subject matter of the claims.

The achievement according to the invention is described hereafter with reference to the apparatus. Features, advantages or alternative embodiments described here can in each case also be transferred to the other subject matter and vice versa. In particular, substantive claims (which are directed at a process, for example) can also be developed with features that are described or claimed in connection with one of the pieces of apparatus. The relevant functional features of the method are embodied by relevant modules or units.

An embodiment of the present invention relates to a patient couch, comprising:
  a docking facility for mechanical docking on a docking point of a medical imaging installation;
  a drive unit including a plurality of wheels for a drive movement of the patient couch up to a docking position, wherein the docking facility reaches the docking point;

at least one sensor, to acquire sensor signals characterizing a relative position between the medical imaging installation and the patient couch;

a computing unit to calculate a movement trajectory with a destination of the docking position for the patient couch, based on the sensor signals acquired; and a display facility, to display the movement trajectory calculated for a user.

An embodiment of the present invention relates to a patient couch, comprising:

a docking facility for mechanical docking on a docking point of a medical imaging installation;

a frame and a plurality of wheels, for drive movement of the patient couch up to a docking position, where the docking facility reaches the docking point;

at least one sensor, to acquire sensor signals characterizing a relative position between the medical imaging installation and the patient couch;

an electronic circuit to calculate a movement trajectory with a destination of the docking position for the patient couch, based on the sensor signals acquired; and a display, to display the movement trajectory calculated.

A further embodiment of the invention relates to a medical imaging system comprising a patient couch according to at least on embodiment of the invention; and a medical imaging installation. The medical imaging installation is used for imaging for medical purposes.

BRIEF DESCRIPTION OF THE DRAWINGS

The aforementioned characteristics, features and advantages of the present invention and the manner in which they are achieved become clearer and more easily comprehensible in conjunction with the description that follows of the example embodiments, which are described in greater detail in connection with the drawing. The invention is not limited to these example embodiments by this description. In various figures identical components are denoted by identical reference characters. The figures are generally not to scale. In the figures.

DETAILED DESCRIPTION OF THE EXAMPLE EMBODIMENTS

Figure 1:
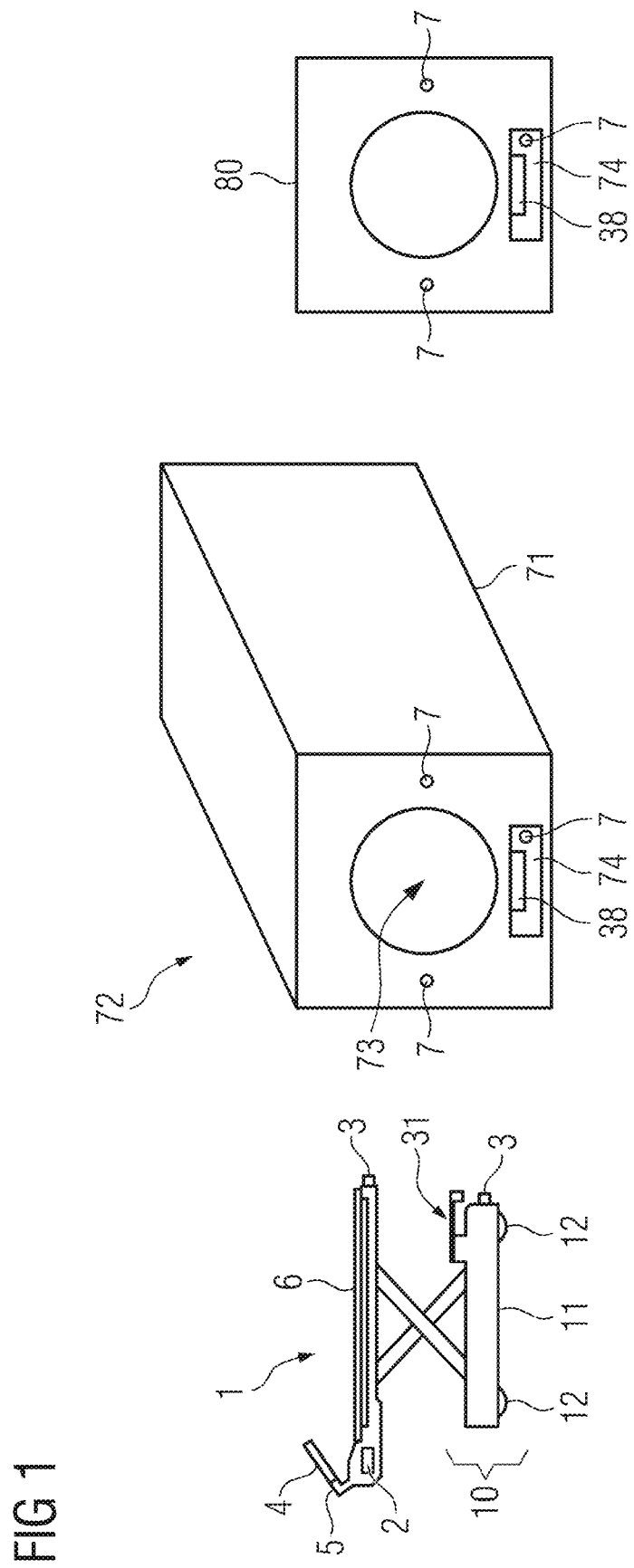
FIG. 1 shows a medical imaging system in an example embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

A first embodiment of the present invention relates to a patient couch, comprising:
  a docking facility for mechanical docking on a docking point of a medical imaging installation;
  a drive unit including a plurality of wheels for a drive movement of the patient couch up to a docking position, wherein the docking facility reaches the docking point;
  at least one sensor, to acquire sensor signals characterizing a relative position between the medical imaging installation and the patient couch;
  at least one processor to calculate a movement trajectory with a destination of the docking position for the patient couch, based on the sensor signals acquired; and a display facility, to display the movement trajectory calculated for a user.

Below it is assumed without loss of generality that the examination subject is a patient, in most cases this being a human. Basically, the examination subject can also be an animal. Therefore, both terms "examination subject" and "patient" are used synonymously. The examination subject can alternatively be a plant or a non-living object, such as a historical artifact or suchlike.

The docking facility of the patient couch of at least one embodiment, interacts with the docking point of the medical imaging installation. Together they form a docking system of a medical imaging system according to at least one embodiment of the invention. By way of the docking system, the patient couch is connected mechanically, electrically and/or by data technology to the medical imaging installation and a precise positioning of the patient couch is achieved, such that a patient who is accommodated on a couch board of the patient couch can be positioned with millimeter-accurate precision in the examination area of the medical imaging installation. Sockets on the patient couch, in the case of a magnetic resonance installation for local coils, for example, are usually connected by cables to the docking system or to the docking facility on the patient couch side of the docking facility, such that measurement signals and/or transmission signals that have been acquired can be transmitted to the medical imaging installation or received by the installation.

The mechanical docking of the patient couch on the medical imaging installation can at the same time comprise the creation of signal and/or power connections to the medical imaging installation. The docking point and docking facility can each comprise docking mechanisms comprising a multiplicity of individual components. In particular, the docking facility comprises a docking pin and the docking point comprises a sliding block guide system. For the docking itself, at least one component of the docking mechanism in the docking facility, the docking pin for example, is mechanically engaged with at least one component of the docking mechanism in the docking point, for example the sliding block guide system. The docking system can additionally comprise a drive unit, in particular a motorized drive unit to generate and/or lock the engagement of the at least two components. The docking system can take the form of any embodiment variants on the docking facility and on the docking point. A possible embodiment variant for the docking system can be seen for example, in the German utility model specification DE 202016007430.

The drive unit of the patient couch according to at least one embodiment of the invention comprises a multiplicity, that is, at least two, preferably at least four, wheels, particularly preferably more than four wheels. The wheels are embodied to facilitate a drive movement of the patient couch, first independent of an operating mode, in particular up to a docking position in which the docking facility reaches the docking point.

The docking position consequently corresponds to a patient couch position, in which the docking facility is arranged so close to and with an orientation to the docking point such that an automatic docking procedure using the docking system can ensue. For example, the docking position can then be reached if the docking pin and sliding block guide system touch each other and are oriented with respect to each other within a permitted tolerance range of from −7° to +7°.

At least four wheels are preferably embodied as freely rotatable casters. These at least four wheels are arranged on the bottom and rigidly on the support facility of the drive unit of the patient couch. The support facility is embodied to support a vertical module of the patient couch on which the horizontal module, comprising a couch board for the patient, is arranged. The vertical module can comprise a lifting mechanism to adjust the height of the horizontal modules, a scissor lift for example. The horizontal module can comprise a propulsion mechanism to, for example, adjust the couch board relative to a support frame of the horizontal module or relative to the remainder of the patient couch horizontally along the longitudinal axis of the patient couch.

Preferably, the four wheels are arranged on the corners, that is, on the corners of the support facility in order to achieve optimum stability of the patient couch. If the patient couch is for example, manually moved by a couch handle arranged transverse to the longitudinal axis of the couch during a manually activated movement due to a drive movement activated manually by a user, the casters advantageously orientate themselves according to the manual set direction and the patient couch moves in the desired direction.

Particularly preferably, the drive unit of the patient couch according to the invention comprises further wheels, as is explained further below.

The sensor unit of the patient couch according to at least one embodiment of the invention is used to acquire at least one, preferably a multiplicity of sensor signals. For this purpose, the sensor unit comprises at least one sensor. Preferably, the sensor unit can comprise a multiplicity of in particular sensors embodied in different ways. The at least one sensor signal acquired identifies a relative position between the medical imaging installation and the patient couch.

In particular, the at least one sensor signal represents a relative position between reference marks arranged in each case on the patient couch and the medical imaging installation. Particularly preferably, the sensor signal identifies a relative position between the reference marks formed by the docking facility and docking point. In particular a plurality of reference marks can be provided on the medical imaging installation, for example, on the gantry of the imaging installation.

The sensor signal can comprise information in the form of a distance and/or of an (angular) position or orientation between the patient couch and medical imaging installation, in particular of the reference marks thereof. The (angular) position or orientation can be formed in particular as a measurement of the angle between the longitudinal axis of the patient couch and the central axis of the imaging installation, for example, in the form of the longitudinal axis of a gantry in the imaging installation.

The patient couch further comprises a computing unit, including an electronic circuit. This unit processes the sensor signals acquired and determines therefrom a movement trajectory for the patient couch.

In at least one embodiment, the movement trajectory identifies a route for the patient couch and comprises as the endpoint or destination of the trajectory the docking position, in which for example, by pressing a button or foot pedal, the docking process can be started. In other words, the movement trajectory describes a movement pathway required to reach a docking position. The movement trajectory consequently describes the route that the patient couch has to take from its current position up to a docking position.

The computing unit according to at least one embodiment of the invention, advantageously comprises an interface equipped to acquire or receive the at least one sensor signal and a calculation unit to calculate the movement trajectory or movement pathway. The computing unit is embodied in particular to generate visual display data for the display facility, based on the calculated movement trajectory.

The computing unit preferably comprises an interface equipped to issue to a display facility the movement trajectory or the visual display data relevant thereto. The receive interface can be embodied as a detached unit separate from the output interface. Both interfaces can also be combined in an interface unit.

Particularly preferably, the interfaces in the computing unit are embodied for optical data communication. If the medical imaging installation is a magnetic resonance installation, interference caused by the data exchange can be prevented in such a way.

The computing unit is advantageously incorporated into the patient couch. The computing unit can alternatively be embodied as or as part of the computing unit of the medical imaging installation. The computing unit can alternatively be arranged apart from or removed from the patient couch or the medical imaging installation, for example, as part of a central computing and control unit of a medical facility such as a hospital. Data exchange then takes place in a cable-free manner.

The patient couch according to according to at least one embodiment of the invention also comprises a display facility. The display facility is embodied to issue the calculated movement trajectory visually for a user. The user addressed is the operator of the patient couch, who moves it to a docking position in a manual operating mode or monitors and/or optionally authorizes the movement procedure according to a (partly) autonomous operating mode.

The display facility is preferably embodied as a display arranged on the patient couch, for example, an LCD display. Since it has to be possible for the user to keep track of the movement trajectory during the entire driving procedure, the display facility is advantageously arranged close to or above the couch handle, which the user touches or holds onto during the movement procedure. The display facility can also be embodied as part of an operating and control interface of the patient couch. It can be embodied in particular as an interactive touch-display, which also serves for receiving control signals at the user end by touch. In alternative embodiments, the display facility can also be embodied as a display that is arranged centrally in the examination room, detached from the patient couch, but visible to the user at any time.

The inventors have therefore realized that through the automatic determination and continuous display of the movement trajectory, the driving of the patient couch up to a docking position can be simplified considerably for the user. Therefore, the determination or estimation of the movement path leading to the docking position by the user can therefore advantageously be avoided. According to the invention, in embodiments according to a manual operating mode, the user only needs to set the direction according to the movement trajectory by applying pressure via the couch handle and specify the speed of movement in order reach the docking position. In other embodiments according to a (partly) autonomous operating mode, the setting of the movement direction and/or speed based on the calculated movement trajectory ensues automatically, optionally after authorization and/or with monitoring on the part of the user.

To monitor the movement, a glance from the user at the display facility is sufficient. A further visual monitoring of the patient couch or of reference marks during the movement can advantageously be avoided. A plurality of repeat actions to achieve the docking position can be avoided, and the imaging workflow can be streamlined. Patient comfort increases.

In a further embodiment of the patient couch according to the invention, the sensor unit is embodied to acquire further sensor signals identifying a current relative position between the medical imaging installation and the patient couch during a movement of the patient couch with the destination of the docking position. Moreover, the computing unit is advantageously embodied to detect a deviation of the current relative position from the movement trajectory and/or a distance of the current relative position from the docking position. In this embodiment, the display facility is further embodied to display to the user the deviation and/or the distance.

In other words, the sensor unit is embodied to repeatedly acquire at least one further, preferably many further, sensor signals while the patient couch is moving in the direction of the docking position and to transmit these signals to the computing unit via the interface. The computing unit is embodied to relate these further sensor signals to the calculated movement trajectory. In particular, the computing unit is embodied to relate them to a docking position. In other words, the computing unit calculates a deviation between the current relative position and the movement trajectory and/or a distance of the current relative position from the docking position. Particularly advantageously, in this embodiment, the display facility is further embodied to likewise display to the user the current relative position and/or the deviation of the same from the calculated movement trajectory and/or the distance from the docking position. Accordingly, the computing unit is embodied to likewise convert these calculated values into visual display data and transmit them via the interface to the display facility or to control the display facility accordingly.

For example, the sensor unit, the computing unit and the display facility can be embodied to acquire, evaluate and display, that is update, the current relative position of the patient couch once every 300 msec, every 500 msec or every second.

In this way, compliance with, or deviation from, the ideal pathway/movement trajectory and the actual pathway is continuously displayed to the user during the driving movement, which facilitates in particular a manual couch movement in a direction or propulsion. As a result thereof, the user has in particular the option of manually reducing the speed of movement when the patient couch is approaching the docking position. The display of the deviation that has been determined or the distance that has been determined can be incorporated into the display of the movement trajectory, for example, the current relative position can be shown by a moving visual colored mark along the movement trajectory, for example, against other representation components. In addition, the calculated deviation from the movement trajectory can be identified as the shortest line on the movement trajectory between the colored mark and the movement trajectory. Alternatively, distances or deviations in further display regions of the display facility can be issued as absolute numerical values.

In a further advantageous embodiment of the patient couch according to the invention, the computing unit is embodied to calculate the movement trajectory such that the longitudinal axis of the patient couch and the longitudinal axis of the medical imaging installation form a maximum angle of 2° between them when the patient couch reaches a docking position. Particularly advantageously, the two longitudinal axes form an angle of 0°. In other words, the computing unit calculates a movement trajectory on the assumption or under the constraint that the patient couch is approaching a docking position such that its longitudinal axes run substantially or completely in parallel. In this embodiment, the two longitudinal axes form a maximum angle of +/−2°. If the patient couch impacts on the medical imaging installation within this tolerance range, a further angle adjustment during the docking procedure can be hardly perceptible to the patient any more or can be avoided completely. Patient comfort increases. Here the longitudinal axis of the medical imaging installation corresponds, for example, to the central axis of the gantry in the imaging facility.

In a further embodiment of the patient couch according to the invention, one wheel of the drive unit is embodied with an adjustable angle between the wheel axis and the longitudinal axis of the patient couch and the computing unit is embodied to generate a control signal for the drive unit to set on the wheel an angle that corresponds to the movement trajectory.

In order to facilitate compliance with the movement trajectory for the user, in this embodiment one wheel in the drive unit is embodied with an adjustable wheel axis. The wheel axis is the wheel's axis of rotation. The drive unit preferably comprises an additional wheel in addition to the four casters, which wheel is arranged on the bottom in a central position of the support unit of the drive unit. This additional wheel is preferably affixed to the support unit by a rotatable securing unit.

The wheel also advantageously comprises an adjustment mechanism, for example, in the form of a motor, in particular in the form of a battery-driven electric motor that acts on the securing unit to adjust a specified actuating angle and, as a result, thereof moves the wheel axis into the desired orientation. The moving of the wheel axis ensues in relation to the longitudinal axis of the patient couch, such that a random angle less than, equal to or greater than 90° can be formed between the wheel axis and the longitudinal axis.

In this embodiment, the computing unit is embodied to calculate a control signal identifying a corresponding actuating angle for the adjustment mechanism, based on the calculated movement trajectory, and transmit the control signal to the adjustment mechanism via the interface. The computing unit is in particular likewise embodied, during the movement of the patient couch, to repeatedly update the control signal and hence the angle of adjustment, based on a calculated deviation or a calculated distance.

The adjustment mechanism is advantageously embodied to adjust the actuating angle in a stationary state or during a driving movement of the patient couch. It is therefore embodied to move the additional wheel against the static friction resistance or rolling resistance of the wheel on the ground. Alternatively, the securing unit and/or the adjustment mechanism can be advantageously embodied to raise the additional wheel from the ground at least during movement. In particular, the adjustment mechanism is embodied to continuously adjust the actuating angle along the movement trajectory according to the control signals from the computing unit. In particular, the adjustment mechanism is embodied to adjust the actuating angle such that, in the vicinity of the docking position, the tolerance range of +/−2° between the longitudinal axes of the patient couch and the medical imaging installation is complied with.

The additional wheel is particularly advantageously arranged centrally between the two rear or the two front casters of the patient couch. Alternatively, the additional wheel can also be positioned at a different point on the support unit. In one embodiment, the additional wheel can likewise be embodied as an adjustable, that is, as a steerable caster. In a different alternative embodiment, one of the four casters arranged on the corners, in particular one of the rear casters can be embodied as an additional, adjustable wheel.

By adjusting the actuating angle on one of the wheels on the drive unit, compliance with the calculated movement pathway or the movement trajectory is simplified, in particular in a manual operating mode. The user now only has to specify the propulsion speed and the adjustable wheel takes over the specification of the direction. A deviation from the movement path in a (partly) autonomous operating mode is advantageously prevented thereby or at least made more difficult.

In a particularly preferred embodiment of the patient couch according to the invention, the adjustment mechanism of the additional wheel is embodied such that it can be deactivated. In other words, an adjustment or a specification of the actuating angle ensues only if necessary, for example, in a drive movement along the movement trajectory and particularly preferably, if the patient couch is embodied for an autonomous movement, as described further below. For example, the adjustment mechanism can be activated based on a control signal identifying a calculated movement trajectory, otherwise it is deactivated. If the adjustment mechanism is inactive, the additional wheel orientates itself passively with a variable angle of adjustment, as do further casters of the drive unit, in the case for example of manual propulsion by the user.

In a preferred embodiment of the patient couch according to the invention, the drive unit comprises a motorized drive unit to drive at least one wheel and the computing unit is embodied to generate a control signal for the drive unit based on the calculated movement trajectory.

In this embodiment, the propulsion force or the movement speed of the patient couch is at least partly, particularly preferably completely, provided by the motorized drive unit. The patient couch is therefore embodied for autonomous movement. In this embodiment, to move the patient couch the user does not need to apply any or, in the case of motorized assistance, only has to apply very little intrinsic force. The drive unit is particularly preferably an electric motor. In this embodiment, the drive unit preferably acts on only one wheel of the drive unit, alternatively a plurality of wheels can be driven. In an advantageous embodiment, the drive unit interacts with a further additional wheel, which is provided with an actuating angle in addition to the four casters and the additional wheel. The further additional wheel is preferably arranged centrally in the middle between the four casters on the bottom on the support unit of the drive unit. The further additional wheel is preferably embodied as a rigid wheel, that is, its axis of rotation cannot, as described in the aforementioned, be moved in relation to the longitudinal axis of the patient couch.

By using an additional wheel with a variable actuating angle in combination with a rigid, motor-driven wheel, the patient couch according to the invention can follow the calculated movement trajectory independently in an autonomous operating mode. Due to the actuating angle for the additional, adjustable wheel being specifiable by the computing unit and updatable, the movement of the patient couch can be complied with precisely up to the docking position. In a manual operation, the user only has to push and therefore specify a forward movement, since the drive unit takes over the "destination-setting" autonomously.

The wheel driven by the drive unit can be embodied to be spring-loaded against the ground below. In this way, uneven areas in the surface beneath can be compensated for. The additional wheel with a variable actuating angle substantially acts as a "rudder" for the direction specification during the driving movement of the patient couch. This embodiment of the patient couch facilitates simple docking since the user does not have to worry about accurate landing at the docking point. As a result thereof, the docking process is facilitated and accelerated. Since the docking position is reached autonomously by the patient couch, the docking process can ensue smoothly. The patient is exposed to considerably fewer jolts. The user is therefore better able to concentrate on the patient and the treatment.

The further additional and powered wheel allows autonomous driving of the mobile patient couch; due to the additional wheel with a variable angle of adjustment, it is possible in addition to specify the movement direction in a simple manner. The patient couch according to the invention is consequently suitable for a purely manual, a motor-assisted, or an autonomous operation.

In one embodiment of the patient couch according to the invention, that is an alternative to the previous embodiment, the drive unit comprises two omni-directional wheels and a motorized drive unit to drive the omni-directional wheels. The computing unit is embodied to generate a control signal for the drive unit based on the calculated movement trajectory. Here too, the drive unit can be embodied as an electric motor.

In addition to the four casters typically provided, this embodiment provides two omni-directional wheels. These are preferably embodied as Mecanum wheels. They are preferably provided centrally in the middle between the four casters on the support unit of the drive unit. One of the wheels can in each case be arranged sideways-on in relation to the longitudinal axis of the patient couch. The omni-directional wheels combine the function of the direction specification and of the couch drive. Accordingly in this embodiment, the computing unit can be embodied to generate control signals for the omni-directional wheels, based on the calculated movement trajectory and/or a distance or a deviation from the movement trajectory or a docking position and transmit the signals to the drive unit of the omni-directional wheels. The control signals also comprise control commands relating to a movement direction and to a movement speed. In this example embodiment, too, the drive unit can advantageously be embodied to comply with the tolerance range of +/−2° with respect to the longitudinal axes of the patient couch and the medical imaging installation as soon as the patient couch approaches the docking position.

In a particularly preferred embodiment of the patient couch according to the invention, the computing unit is embodied to adjust a control signal for one of the aforementioned drive units as a function of the distance, determined by the sensor unit, between the current relative position and the docking position, such that the movement speed is reduced when the distance falls below a previously defined threshold value.

In other words, if the patient couch approaches the docking position along the movement trajectory and if the distance falls below a previously defined threshold value, for example, 50 cm, 20 cm, or 10 cm, the movement speed of the patient couch generated by the drive unit is adjusted to a speed value that falls below a previously defined maximum speed threshold value. The previously defined maximum speed threshold value is defined such that, even on short routes, direction adjustments of the patient couch by the adjustment mechanism or drive unit can still be achieved comfortably insofar as deviations from the movement trajectory might occur before the docking position is reached, and/or the tolerance range of +/−2° has not yet been reached with respect to the angular orientation of the patient couch and the medical imaging installation.

In particular, a plurality of distance intervals with corresponding movement speeds can be provided, such that the movement speed drops further, the closer the patient couch is to the docking position.

In a different embodiment of the patient couch according to the invention, the sensor unit comprises at least one from the group of sensors that follows: optical sensor, acoustic sensor, acceleration sensor, magnetic field sensor, revolution counter.

An optical sensor can be embodied for example, as a laser scanner or as a 2D- or 3D-camera, both optical sensors being embodied to scan the environment in particular according to the reference marks referred to in the aforementioned, for example, in the form of detection patterns that are affixed to the medical imaging installation and/or the docking point. The optical sensors can also be embodied to determine a three-dimensional environment model and transmit model data for a calculation of the movement trajectory to the computing unit. By evaluating distance, size and/or shape of reference marks, a location can be determined in particular using a 2D-camera.

Alternatively, for medical imaging installations in the form of a magnetic resonance tomography installation, the sensor unit can comprise a magnetic field sensor to detect a static magnetic field in the environment of the patient couch in order to locate the patient couch relative to the magnet. For this purpose, the sensor unit can comprise one or a plurality of magnetic field sensors (for example, Hall effect sensors) on the patient couch, which determine the strength and direction of the magnetic field and in combination with the course of the field lines that is known for the specific installation, can determine the location for the patient couch.

Alternatively, an acoustic sensor in the form of an ultrasound transmitter and receiver, which sensor is embodied to carry out a transit time measurement of sound waves, can be provided. For synchronizing between the ultrasound transmitter and receiver, an optical signal parallel to the ultrasound route can be used. Alternatively, for one of the wheels in the drive unit, the route covered with respect to a previously determined reference position (for example, a resting or loading station of the patient couch), the relative change in position and hence the relative position with respect to the docking position of the patient couch can be determined (through odometry) by a sensor in the form of a revolution counter.

In a further embodiment of the patient couch according to the invention, at least one sensor in the sensor unit has the same orientation as the docking facility. The docking facility is preferably arranged on the front of the patient couch. The front corresponds to the end of the patient couch that lies opposite the end on which the operating handle and/or the display unit is arranged for the user. In other words, both the sensor and the docking facility are therefore oriented in the movement direction according to the movement trajectory. This results for the at least one sensor in a field of view that encloses the medical imaging installation, the docking position, the docking point or corresponding reference marks. This advantageously ensures that, during a movement of the couch along the calculated movement trajectory, the sensor unit can repeatedly and continually acquire sensor signals and forward them to the computing unit.

In a further embodiment of the patient couch according to the invention, at least one sensor in the sensor unit is embodied with a sensitive field of view, which is at least 1 m long and/or forms an angle of +/−30°. The field of view of the sensor is preferably embodied to be greater in length and/or angular range, for example, 1.5 m, 2 m, 2.5 m, +/−40°, +/−45°, +/−50°, +/−60°. In other words, the field of view of the sensor extends for at least 1 m in the movement direction or directed towards the front along the longitudinal axis of the patient couch and forms an angular range of +/−30° starting from the longitudinal axis of the patient couch. Reference marks that are located inside the field of view of the sensor can therefore be acquired.

The at least one sensor is embodied in particular to detect reference marks identifying the docking point on the medical imaging installation inside the field of view. Accordingly, the computing unit is embodied to determine the location and/or the position of the docking point in relation to the current couch position, that is to determine a current relative position.

A further embodiment of the invention relates to a medical imaging system comprising a patient couch according to at least on embodiment of the invention; and a medical imaging installation. The medical imaging installation is used for imaging for medical purposes.

The medical imaging installation, in at least one embodiment, is equipped in particular to generate image data using optical radiation, electromagnetic radiation and/or X-rays. The medical imaging installation can be embodied as an x-ray installation, as a computer tomography unit, as a positron emission tomography unit, an ultrasound installation or such like.

In a particularly preferred embodiment of the invention, the medical imaging installation is embodied as a magnetic resonance installation. On its gantry, the medical imaging installation preferably comprises a docking point for the patient couch.

The medical imaging system can comprise further components. In particular the medical imaging system can also comprise a docking station for the patient couch, on which the patient couch can dock when not in use. For this purpose, a docking point can also be provided on the docking station, which point can interact with the docking facility of the patient couch in a comparable manner to the docking system described in the aforementioned. When not in use, in a docked state on the docking station, the patient couch can be supplied with energy via a corresponding interface of the docking system. In particular, a battery system, for example, a lithium-ion battery of the patient couch, can be charged there. In particular, the battery system can be used to supply the aforementioned components such as the sensor unit, computing unit, display unit, adjustment mechanism and/or the drive units.

To sum up, at least one embodiment of the present invention is based on a combination of sensors, a computing unit and a display unit. It preferably also comprises actuator technology to implement a navigation function for a patient couch. The navigation function can be activated for a purely manual, a partly manual or a fully automatic/autonomous operation of the patient couch. In particular, the navigation function can be turned off when it is not required.

The navigation function described can also be implemented for other medical units or comparable mobile medical devices in addition to the patient couch. Both the passive display of the calculated movement trajectory and the active direction specification by way of an additional wheel with a variable angle of adjustment, alone or in combination with the display of the current distance, allow a considerably more precise and more gentle approach of the couch onto the docking station by the operator and consequently reduce the stress for the patient considerably. The workflow in the medical facility is improved, and collisions due to an incorrect approach can be avoided.

FIG. 1 shows a medical imaging system 72 according to the invention in an example embodiment. The system 72 comprises a patient couch 1 and a medical imaging installation 71 in the form of a magnetic resonance installation or the gantry of the same. In this embodiment the system also comprises a docking station 80.

The patient couch 1 basically has a conventional design. It comprises a horizontal module comprising a couch board 6 for accommodating and positioning a patient. The horizontal module also comprises an operating handle 5 on the rear end of the patient couch 1. Via the operating handle 5, a user of the patient couch can apply a propulsion force to effect a change of direction and/or effect an authorization of an autonomous movement.

For this purpose, the operating handle 5 can particularly advantageously be embodied, for example, to be force, pressure- or touch-sensitive by way of capacitive sensors. On the operating handle 5 or in the direct vicinity thereof, the horizontal module also comprises a display unit 4. The display unit 4 is embodied such that, during a movement of the patient couch 1 and by touching the operating handle 5, the user can directly see and observe the display unit 4. The display unit 4 is used according to an embodiment of the invention to display a movement trajectory that has been calculated for the patient couch. It can also be used to display a deviation and/or a distance of a current relative position of the patient couch 1 with respect to the movement trajectory or the distance between the current position of the patient couch and the docking position. The display unit 4 can be, for example, an LCD, plasma or OLED screen. Furthermore, it can be a touch-sensitive screen, which is also embodied as an input unit of a control and operating interface of the patient couch 1.

The patient couch also comprises a drive unit 10 with a support unit 11 in the form of a supporting frame. First, the supporting frame 11 forms the base plate for the patient couch 1, on which the vertical module of the patient couch and on this in turn, the horizontal module, is arranged. Second, the support unit 11 forms the connection between the patient couch 1 and the ground, for example, the floor of the treatment room.

For this purpose, wheels or caster elements, here in the form of passive casters 12, are arranged on the support unit, via which moving or driving the patient couch 1 becomes possible. The casters 12 are oriented according to a predetermined propulsion direction.

On the support unit 11, at the end opposite to the operating handle 5, that is, on the anterior region of the patient couch 1, a sensor unit comprising at least one sensor 3, here two sensors 3, is provided. The sensor unit is used for acquiring sensor signals, which comprise information regarding a relative position of the patient couch 1 with respect to the medical imaging installation 71.

In this embodiment, the sensor unit is embodied with a field of view that encloses the environment in front of the patient couch 1. In this example embodiment, the sensor unit comprises two laser scanners 3, which scan the environment in front of the patient couch 1. In this embodiment the sensors 3 are embodied as optical sensors in the form of laser scanners, with a sensor 3 being arranged on the horizontal module and a sensor on the support unit 11, that is, arranged close to the ground. However, alternative types of sensor can also be used. The field of view of the sensors extends at least as far as 1 m and forms an angle of view of +/−30° starting from the longitudinal axis of the patient couch 1. Their field of view is preferably greater. In particular, the sensors 3 are embodied to detect reference marks 7 that are arranged on the medical imaging installation 71, but also on the docking station 80 or on another random position in the environment of the patient couch 1. In particular, the reference marks can also be provided on the docking point 74 or by components of the same.

The sensor signals from the sensor unit can be transmitted via an interface (not shown) on a computing unit 2 of the patient couch 1. Here, the computing unit 2 is arranged in the horizontal module in the vicinity of the display unit 4 and the operating handle 5. The computing unit 2 is used for evaluating the sensor signals acquired, for calculating a movement trajectory B for the patient couch 1 up to a docking position, for calculating a distance of a current relative position from the movement trajectory or suchlike, and for generating control signals for the drive unit 10 or of display data for the display unit 4, based on the sensor signals, as explained in greater detail further below.

The computing unit 2 is in each case in data exchange via the interface with the drive unit 11, optionally with individual sub-components thereof, with the sensor unit and/or the display unit 4. A data exchange according to an embodiment of the invention preferably ensues via communication protocols or standards that are basically known. The interface can be embodied as a hardware and/or software interface. Data transmission between two units or system components can ensure in a bidirectional or a unidirectional manner. For example, the computing unit 2 can be embodied as an electronic circuit such as, for example, a so-called FPGA (Field Programmable Gate Array) or an arithmetic logic unit; or can include at least one processor for example. The computing unit 2 can alternatively be arranged outside the patient couch 1. Particularly preferably, the interface allows an optical data exchange, such that for example a magnetic field of the medical imaging installation 71 is not disrupted.

Furthermore, a docking facility 31 is arranged on the support unit 11 of the drive unit 10, with which the patient couch can dock on a docking point 74 of the imaging facility 71. The docking point 74 comprises a docking mechanism 38, which interacts with the docking mechanism 36 on the docking facility.

The docking station 80 also features a corresponding docking point 74. In each case, a docking point 74 and the docking facility 31 together form a docking system. A docking system is described in further detail in relation to FIG. 2.

While the patient couch 1 approaches the magnetic resonance installation 71 when a medical image generation is to be carried out for a patient, the docking station 80 is approached when the magnetic resonance installation 71 or the patient couch 1 is not in use. Via the docking station 80, a battery system 29 of the patient couch 1 can be charged outside its operating times, for example. In addition, the docking station 80 offers a defined location for the patient couch 1 outside its operating times.

Furthermore, the magnetic resonance installation 71 has a patient recess 73 in the form of a round, cylindrical-shaped aperture, into which the couch board 6 of the patient couch 1 can be at least partly driven by way of a horizontal adjustment facility for image generation when the patient couch 1 is connected by way of the docking facility 31 to the docking point 74 on the magnetic resonance installation 71.

Figure 2:
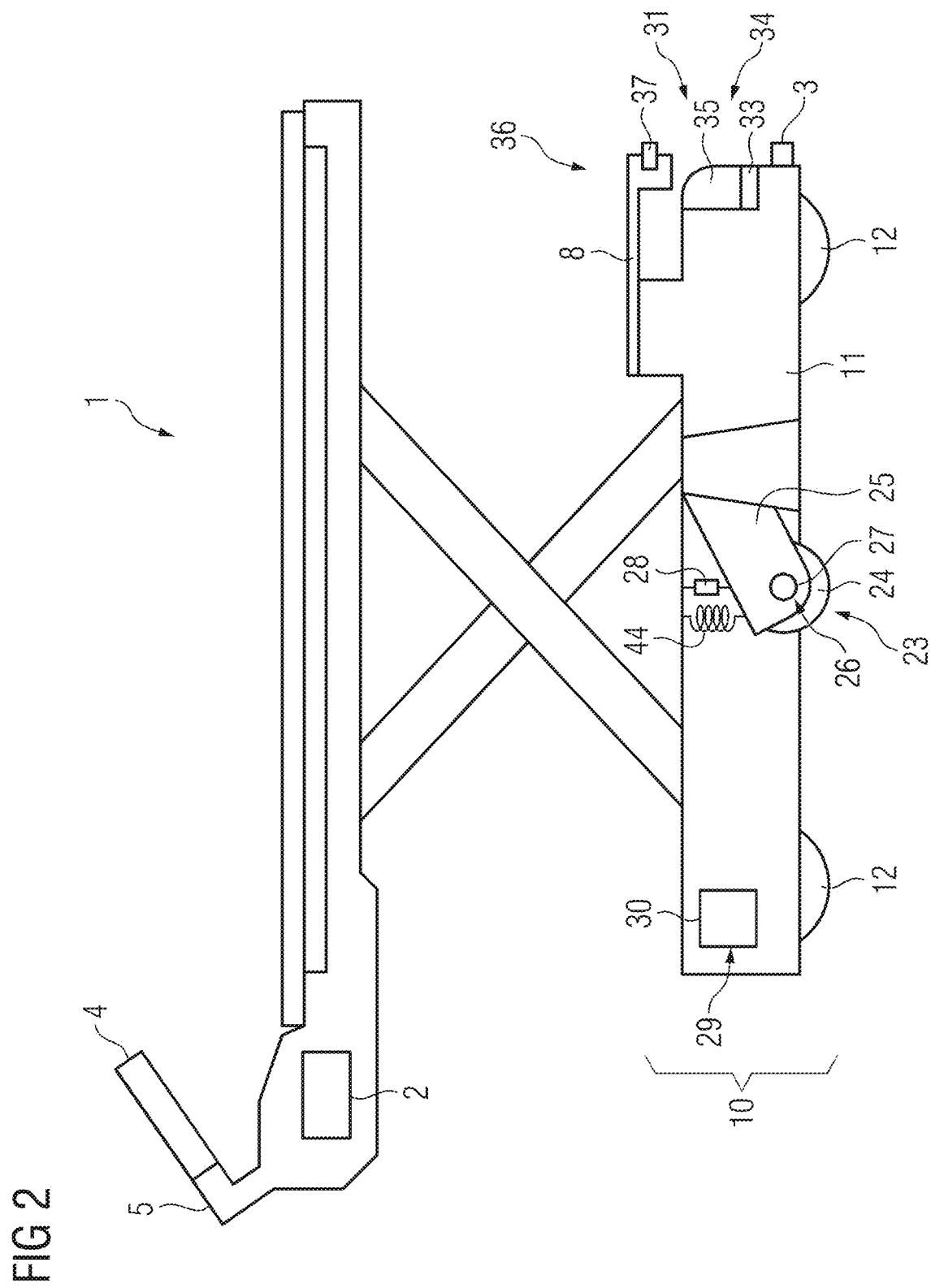
FIG. 2 shows a patient couch in cross section in an example embodiment of the invention.

FIG. 2 shows a patient couch according to an embodiment of the invention in cross section in an example embodiment of the invention. On the support unit 11 of the drive unit 10, the docking facility 31 is arranged at the front. The docking facility 31 comprises a docking pin 8 with the docking mechanism 36 at the docking facility end, which mechanism in the present case has a protruding engaging element 37 in the form of a caster, which is to be inserted into a sliding block guide system of a docking mechanism 38 at the docking point end in order to pull the patient transport facility 1 to complete a docking procedure onto the docking point 74 and also to establish the power and data connections of an interface facility 34 of the docking facility 31. The interface facility 34 comprises a data interface 35 and also an energy interface 33, for example in the form of a 48V energy interface.

On the medical imaging installation 71 or the docking station 80, electric power provided to and supplied via the energy interface 33 can be used, in the docked state, directly for operating the electrical consumers, for example, computing unit 2 or display unit 4, of the patient couch 1, or for charging the battery system 29 together with the lithium ion batterie 30. Lithium ion batteries have a high specific energy. However, they are compact and of rather light weight, such that they can, particularly advantageously, be used inside the patient couch according to an embodiment of the invention. Moreover, they also have a good magnetic field tolerance. Generally speaking, the electrical energy source, in particular the rechargeable battery, can preferably be mounted in the support unit 11 on the bottom.

In this example embodiment, the patient couch 1 has an additional wheel arrangement 23, arranged centrally in the middle between the four wheels 12 arranged on the corners in the form of casters in the support unit 11, which arrangement is embodied to assist a manual movement of the patient couch 1 or to move the patient couch 1 without exerting any manual force. The additional wheel arrangement 23 has an additional wheel 24, which is arranged on a holder 25 and is embodied here as a hub motor 27 and can be driven via a drive unit 26. The holder 25 is pivotably mounted in the support unit 11 via a spring 44.

Against the force of the spring 44, an electrically powered lowering mechanism 28 can bring the additional wheel 24 into an operating position with floor contact. In this case, the holder 25 is therefore lowered with the additional wheel 24. To lift the additional wheel 24, the lowering mechanism 28 can be released such that the spring 28 swivels the additional wheel 24 upwards again out of the operating position; provision can also be made, however, for the lifting to ensue in a controlled manner via an operation of the lowering mechanism 28. The additional wheel 24 is oriented in the longitudinal direction of the patient couch 1 and is in particular not steerable.

At the front, on the support unit 11, the patient couch 1 comprises two acoustic sensors 3 in the form of ultrasound receivers, which interact with reference marks on the medical imaging installation 71 and/or the docking station 80 in the form of ultrasound transmitters 7. The ultrasound receivers 3 can be synchronized with the ultrasound transmitters 7 via further optical signal generators. The ultrasound signals received are transmitted by the sensors 3 to the computing unit 2. From them the computing unit 2 determines a relative position of the patient couch 1 with respect to the installation 71 or to the docking station 80 and calculates a movement trajectory B from them. This identifies the route for the patient couch 1 with the destination of a docking position. In the docking position, the docking mechanisms of the docking facility 31 and the docking point 74 are arranged so close together and oriented such that an automatic docking procedure can be started. Particularly advantageously, the movement trajectory is determined such that the patient couch 1 reaches with an angle less than +/−2° in order to avoid a further automatic angular orientation to 0°. The calculated movement trajectory is converted by the computing unit 2 into visual display data, transmitted to the display unit 4 and displayed there for the user.

Figure 3:
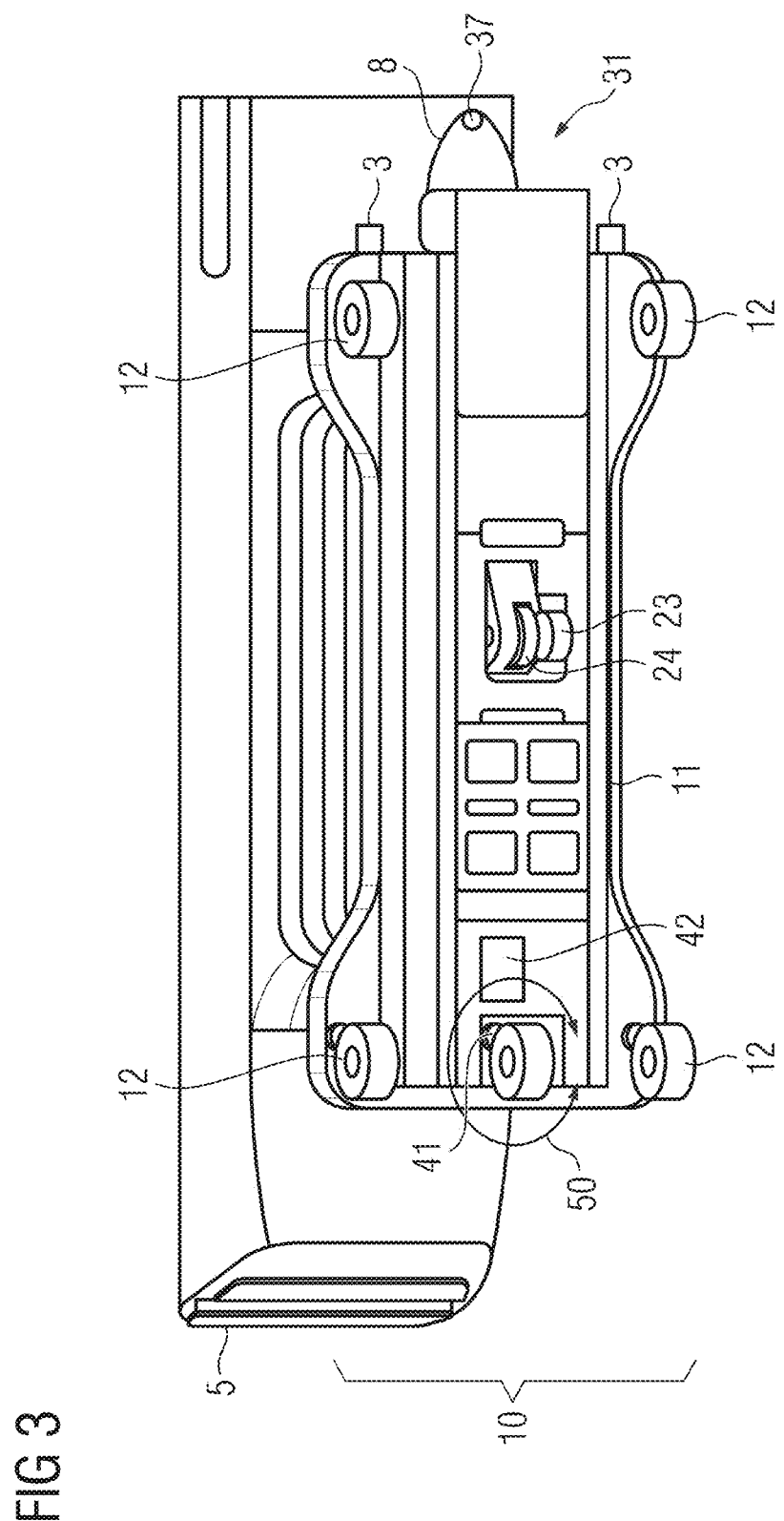
FIG. 3 shows a patient couch in a further example embodiment of the invention in a perspective view from below.

FIG. 3 shows the patient couch 1 in a further example embodiment in a perspective view from below. In addition to the additional wheel arrangement 23, a further additional wheel 50, which is arranged in the middle between the two rear casters 12, is visible. The additional wheel 50 is steerable in the sense that its actuating angle is embodied to be variable and adjustable (marked by the arrows). The additional wheel 50 is fixed to the support unit 11 by way of the fixing device 41, in the form of a controllable swivel joint. The swivel joint 41 can be moved in a motorized manner by way of the adjustment mechanism 42 and therefore the additional wheel 50 can be brought into a desired angular position, in particular corresponding to the movement trajectory B and/or to a current relative position of the patient couch 1. The adjustment mechanism 42 is embodied to receive and convert control signals from the computing unit 2. In particular, the adjustment mechanism 42 is embodied to repeatedly adjust the actuating angle of the additional wheel 50 during a movement of the patient couch 1 up to a docking position in order to implement the movement along the movement trajectory B.

If no movement trajectory B is available for the patient couch 1 at a time, the engagement between the securing unit 41 and the adjustment mechanism 42 by way of a coupling element provided between them can be decoupled. The fixing device 41 is then in particular freely rotatable, corresponding to a passive caster 12.

The combination of the additional wheel arrangement 23 and the additional wheel 29 together with the sensor unit and computing unit 2 according to this example embodiment allows an autonomous 'tracking' and moving of the patient couch 1. Here, in the optimum scenario, all the user needs is an authorization by touching the operating handle 5 and also a visual monitoring of the movement on the display unit 4.

Figure 4:
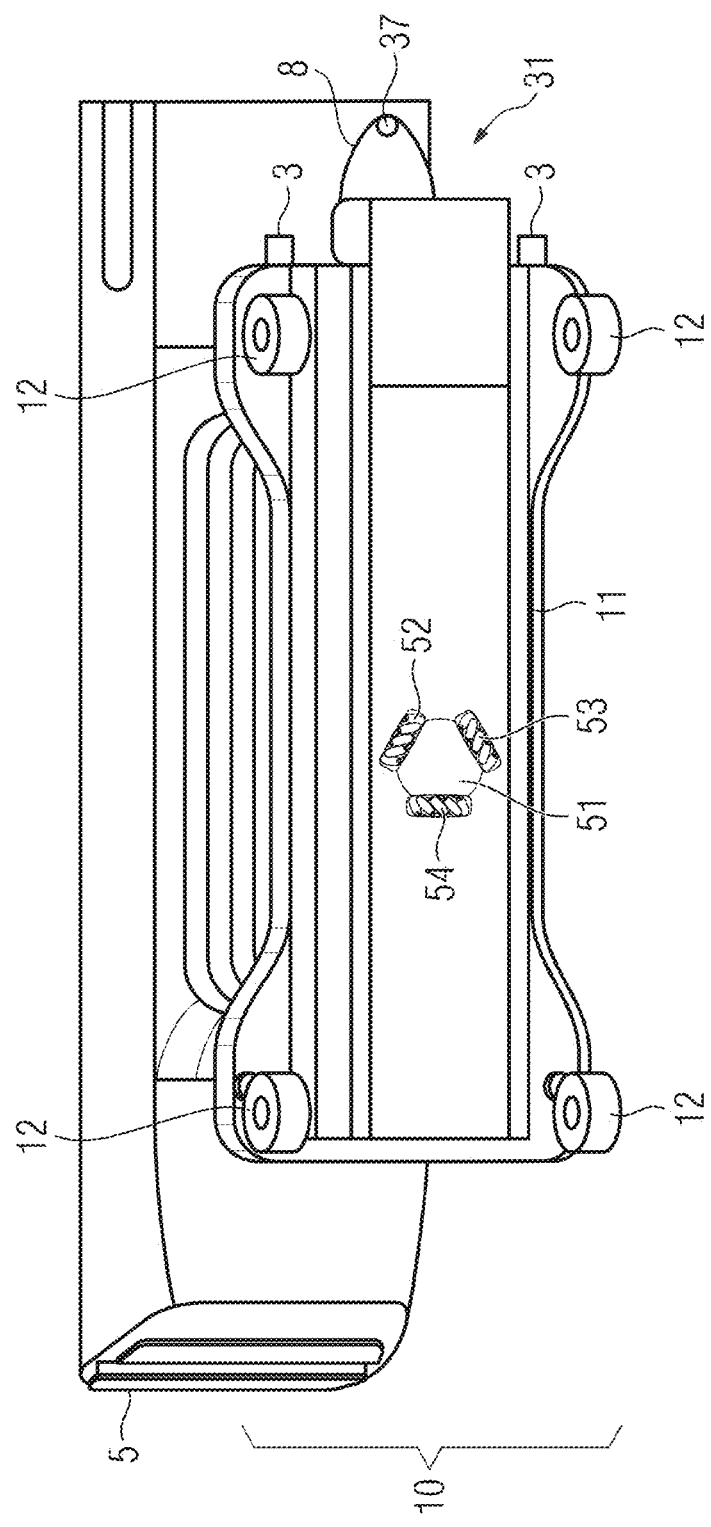
FIG. 4 shows a patient couch in a further example embodiment of the invention, likewise in a perspective view from below.

FIG. 4 shows a further example embodiment of the patient couch 1 according to the invention in a perspective view from below. In this embodiment, instead of the additional wheel arrangement 23 and the further additional wheel 50, centrally in the middle between the casters 12 there are provided two omni-directional wheels 52, 53, in the form of Mecanum wheels, which are driven by the drive unit 51, which is in the form of a motor. The remaining components of the patient couch 1 can be embodied in an identical manner to the example embodiment in FIG. 3. In particular, the computing unit 2 is embodied to generate control signals relating to the direction to be set and relating to the propulsion speed corresponding to the calculated movement trajectory for the drive unit 51 and transmit them to the unit via the interface. Due to being embodied by way of spherical casters inclined at a 45° angle, the Mecanum wheels 52, 53 can assume both the drive function of the additional wheel arrangement 23 and also the direction function of the further additional wheel 50 of the previous example embodiment.

Therefore, in this example embodiment too, a substantially autonomous driving operation for the patient couch 1 with a tracking function is possible.

Figure 5:
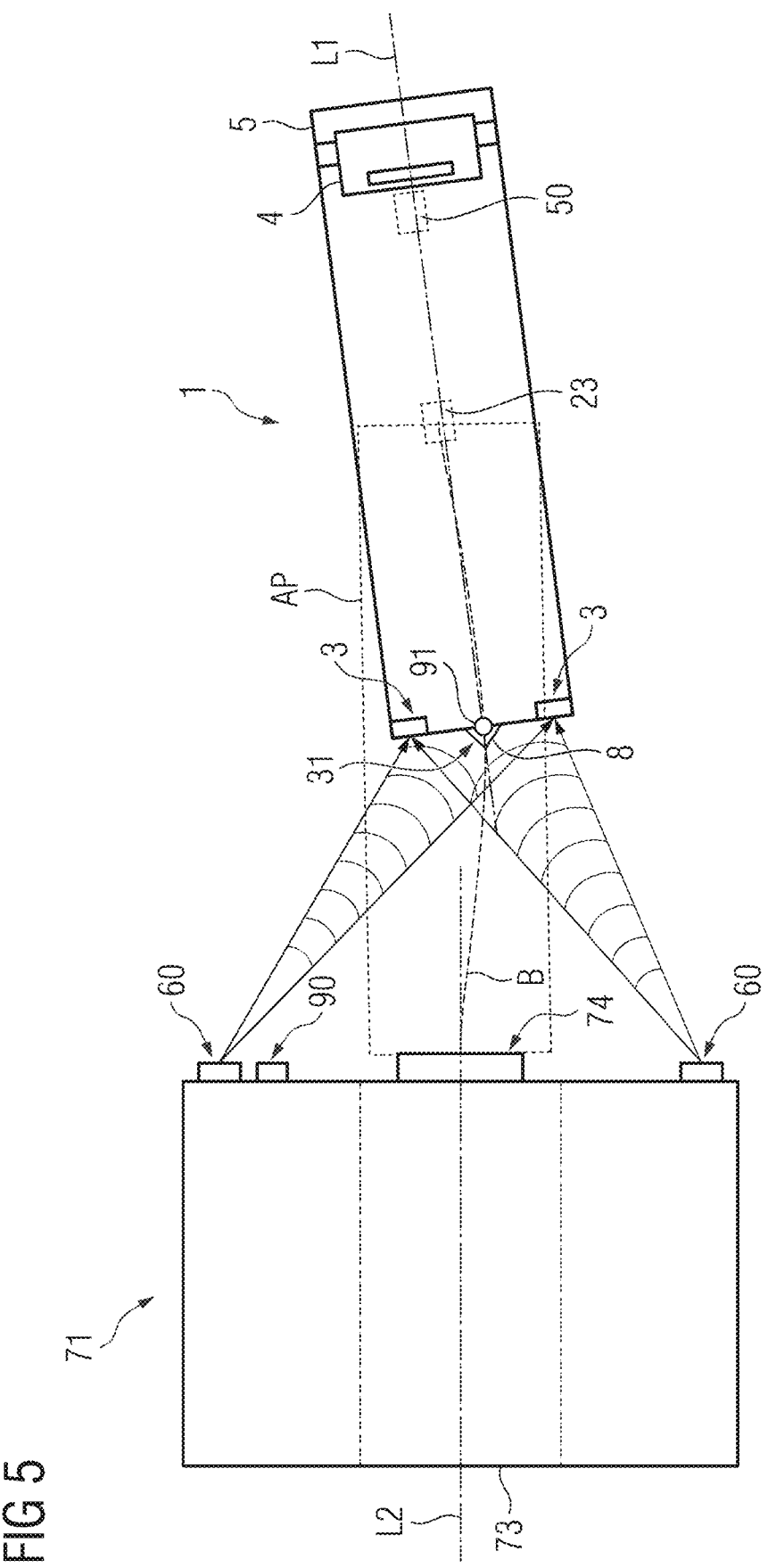
FIG. 5 shows a medical imaging system in a further example embodiment of the invention in a top view.

FIG. 5 again shows, in a further example embodiment, a medical imaging system according to the invention 72 in a top view. The patient couch 1 is on the way to a medical imaging installation 71 along the movement trajectory B. The destination of the movement trajectory B is the docking position AP, in which the docking pin 8 of the docking facility 31 reaches the docking point 74 such that an automatic docking procedure can be started.

By way of the additional wheel arrangement 23 and the steerable additional wheel 50, the patient couch 1 proceeds along the calculated movement trajectory B. The movement trajectory B is advantageously calculated by the computing unit 2 (not shown here), such that the longitudinal axes L1 and L2 of the patient couch 1 and the imaging facility 72 at the end of the movement trajectory form an angle less than 7°, and particularly preferably an angle less than 2°, in order to allow jolt-free docking. The movement trajectory B is displayed on the display unit 4.

The computing unit 2 determines the movement trajectory B based on sensor signals, which are acquired by the sensors 3, here in the form of acoustic ultrasound sensors. Each of the ultrasound sensors 3 is embodied to receive ultrasound signals from two ultrasound transmitters 60 located on the imaging installation 72. Due to the position of the patient couch 1, differences in transit time emerge between the receivers 3 for the signals received from one of the transmitters 60. Via an optical synchronization system 90, 91, here in the form of an infrared photodiode 90 and on the infrared emitter 91, a synchronization of the sensors 3 and the ultrasound transmitters 60 can advantageously ensue. Via an evaluation of the running time, the computing unit 2 can determine a current relative position of the patient couch 1 and on the basis thereof and optionally of the calculated movement trajectory B, can determine a current deviation or a current distance from the imaging facility 72. This information too can be displayed to the user via the display unit 4.

If the patient couch 1 is already moving along the movement trajectory B, the computing unit 2 generates control signals for the adjustment mechanism 42 of the additional wheel 50, according to the current relative position in order to continue the movement along the movement trajectory B. If a deviation from the movement trajectory B is detected, a control signal is calculated according to a correcting actuating angle for the additional wheel 50 and sent to the adjustment mechanism 42. In addition, the computing unit 2 can also provide a control signal for the drive unit 27 of the additional wheel arrangement 23, which signal identifies the propulsion speed of the patient couch 1 in an autonomous operation of the couch. In particular, this control signal can be adjusted to a current distance of the patient couch 1 from the imaging facility 72 and reduce the drive force, the closer the patient couch 1 comes to the imaging facility 72.

Although the invention has been illustrated and described in greater detail by the preferred example embodiment, the invention is not restricted to the details disclosed and other variants can be derived therefrom by the person skilled in the art without going beyond the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A patient couch comprising:
   a docking device configured to mechanically dock to a docking point of a medical imaging installation;
   a drive unit, including a plurality of wheels, configured to drive movement of the patient couch up to a docking position at which the docking device reaches the docking point;
   at least one sensor configured to acquire sensor signals characterizing a relative position between the medical imaging installation and the patient couch;
   a computing unit configured to calculate, based on the sensor signals, a movement trajectory with a destination of the docking position for the patient couch, wherein
      the computing unit is configured to calculate the movement trajectory such that a longitudinal axis of the patient couch and a longitudinal axis of the medical imaging installation form a maximum angle of 2° with respect to one another when the patient couch reaches the docking position; and
   a display device configured to display the movement trajectory.

2. The patient couch of claim 1,
   wherein a wheel, of the plurality of wheels of the drive unit, has an adjustable angle between a wheel axis and the longitudinal axis of the patient couch; and
   wherein the computing unit is configured to generate, for the drive unit, a control signal to adjust the adjustable angle corresponding to the movement trajectory.

3. The patient couch of claim 1, wherein the drive unit comprises:
   a motorized driver configured to drive at least one wheel, of the plurality of wheels, and wherein
   the computing unit is configured to generate a control signal for the motorized driver, based on the movement trajectory.

4. The patient couch of claim 1,
   wherein the plurality of wheels includes two omni-directional wheels;
   wherein the drive unit includes a motorized driver configured to drive the two omni-directional wheels; and
   wherein the computing unit is configured to generate a control signal for the motorized driver, based on the movement trajectory.

5. The patient couch of claim 1, wherein the drive unit comprises:
   a motorized driver configured to drive at least one wheel, of the plurality of wheels; and wherein
   the computing unit is configured to
      generate, for the motorized driver, a control signal based on the movement trajectory, and
      adjust the control signal for the motorized driver as a function of the distance between the docking position and a current relative position between the medical imaging installation and the patient couch, such that a speed of movement is reduced when the distance falls below a threshold value.

6. The patient couch of claim 1, wherein the at least one sensor comprises at least one of an optical sensor, an acoustic sensor, an acceleration sensor, a magnetic field sensor, or a revolution counter.

7. The patient couch of claim 1, wherein the at least one sensor has a same orientation as the docking device.

8. The patient couch of claim 1, wherein the at least one sensor has a sensitive field of view, the sensitive field of view being at least one of at least 1 m long or forming an angle of +/−30°.

9. A medical imaging system comprising:
   the patient couch of claim 1; and
   the medical imaging installation.

10. The medical imaging system of claim 9, wherein the medical imaging installation is a magnetic resonance installation.

11. A patient couch, comprising:
    a docking device configured to mechanically dock to a docking point of a medical imaging installation;
    a drive unit, including a plurality of wheels, configured to drive movement of the patient couch up to a docking position at which the docking device reaches the docking point;
    at least one sensor configured to acquire sensor signals characterizing a relative position between the medical imaging installation and the patient couch, the sensor signals including a measurement of an angle between a longitudinal axis of the patient couch and a central axis of the medical imaging installation;
    a computing unit configured to calculate, based on the sensor signals, a movement trajectory with a destination of the docking position for the patient couch; and
    a display device configured to display the movement trajectory, wherein
       the at least one sensor is part of a sensor unit,
       the sensor unit is configured to, during movement of the patient couch it the destination of the docking position, acquire further sensor signals identifying a current relative position between the medical imaging installation and the patient couch,
       the computing unit is configured to detect at least one of a deviation of the current relative position from the movement trajectory or a distance of the current relative position from the docking position,
       the display device is configured to display at least one of the deviation or the distance, and the computing unit is configured to calculate the movement trajectory such that the longitudinal axis of the patient couch and a longitudinal axis of the medical imaging installation form a maximum angle of 2° with respect to one another when the patient couch reaches the docking position.

12. The patient couch of claim 11,
wherein a wheel, of the plurality of wheels, has an adjustable angle between a wheel axis and the longitudinal axis of the patient couch; and
wherein the computing unit is configured to generate, for the drive unit, a control signal to adjust the adjustable angle corresponding to the movement trajectory.

13. The patient couch of claim 11, wherein the drive unit comprises:
a motorized driver configured to drive at least one wheel, of the plurality of wheels, and wherein
the computing unit is configured to generate a control signal for the motorized driver, based on the movement trajectory.

14. The patient couch of claim 11,
wherein the plurality of wheels includes two omni-directional wheels;
wherein the drive unit includes a motorized driver configured to drive the two omni-directional wheels; and
wherein the computing unit is configured to generate a control signal for the motorized driver, based on the movement trajectory.

15. A patient couch, comprising:
a docking device configured to mechanically dock to a docking point of a medical imaging installation;
a frame and a plurality of wheels configured to drive movement of the patient couch up to a docking position at which the docking device reaches the docking point;
at least one sensor configured to acquire sensor signals characterizing a relative position between the medical imaging installation and the patient couch, the sensor signals including a measurement of an angle between a longitudinal axis of the patient couch and a central axis of the medical imaging installation;
an electronic circuit configured to calculate, based on the sensor signals, a movement trajectory with a destination of the docking position for the patient couch; and
a display configured to display the movement trajectory,
wherein
the electronic circuit is configured to calculate the movement trajectory such that the longitudinal axis of the patient couch and longitudinal axis of the medical imaging installation form a maximum angle of 2° with respect to one another when the patient couch reaches the docking position.

16. The patient couch of claim 15, wherein the electronic circuit includes at least one processor.

17. The patient couch of claim 15, wherein the electronic circuit includes a Field Programmable Gate Array (FPGA).

18. A medical imaging system comprising:
the patient couch of claim 15; and
the medical imaging installation.

19. The patient couch of claim 15,
wherein a wheel, of the plurality of wheels, has an adjustable angle between a wheel axis and the longitudinal axis of the patient couch;
wherein the patient couch includes a driver; and
wherein the electronic circuit is configured to generate, for the driver, a control signal to adjust the adjustable angle corresponding to the movement trajectory.

20. The patient couch of claim 15, further comprising:
a motorized driver configured to drive at least one wheel, of the plurality of wheels; and wherein
the electronic circuit is configured to generate a control signal for the motorized driver, based on the movement trajectory.

21. The patient couch of claim 15,
wherein the plurality of wheels includes two omni-directional wheels;
wherein the patient couch includes a motorized driver configured to drive the two omni-directional wheels; and
wherein the electronic circuit is configured to, based on the movement trajectory, generate a control signal for the motorized driver.

* * * * *